US009186073B2

(12) United States Patent
Petrucelli

(10) Patent No.: US 9,186,073 B2
(45) Date of Patent: *Nov. 17, 2015

(54) REMOVABLE HANDHELD UNIT

(75) Inventor: Steven Petrucelli, Cranbury, NJ (US)

(73) Assignee: Measurement Ltd., Grand Cayman (KY)

( * ) Notice: Subject to any disclaimer, the term of this patent is extended or adjusted under 35 U.S.C. 154(b) by 1139 days.

This patent is subject to a terminal disclaimer.

(21) Appl. No.: 13/016,679

(22) Filed: Jan. 28, 2011

(65) Prior Publication Data
US 2011/0196617 A1 Aug. 11, 2011

Related U.S. Application Data

(63) Continuation-in-part of application No. 12/942,688, filed on Nov. 9, 2010, now Pat. No. 8,265,901, which is a continuation of application No. 11/985,345, filed on Nov. 14, 2007, now Pat. No. 7,831,408.

(60) Provisional application No. 60/859,221, filed on Nov. 15, 2006.

(51) Int. Cl.
G01G 19/44 (2006.01)
A61B 5/022 (2006.01)
A61B 5/053 (2006.01)
(Continued)

(52) U.S. Cl.
CPC .............. *A61B 5/022* (2013.01); *A61B 5/0537* (2013.01); *A61B 5/4869* (2013.01); *A61B 5/4872* (2013.01); *A61B 5/742* (2013.01); *G01G 19/50* (2013.01); *G01G 23/3728* (2013.01);
(Continued)

(58) Field of Classification Search
CPC . G01G 19/44; G01G 19/414; G01G 19/4146; G01G 19/50; G01G 23/00; G01G 23/3728; G01G 9/00; G01C 22/06; G06F 19/00; G06F 19/3728; G06F 19/3406; A61B 5/00; A61B 5/0002; A61B 5/0024; A61B 5/0537; A61B 5/11; A61B 5/1118; A61B 5/4869; A61B 5/4872; A61B 5/6887
USPC ......... 702/104, 130–132, 173, 188–190, 127, 702/138–139, 141, 160; 177/1–5, 177/25.11–25.13, 25.16, 25.19; 600/301
See application file for complete search history.

(56) References Cited

U.S. PATENT DOCUMENTS 6,790,178 B1 * 9/2004 Mault et al. ................... 600/300
7,831,408 B2 * 11/2010 Petrucelli ...................... 702/173
(Continued)

OTHER PUBLICATIONS

Hamaguchi et al., User Localization Using Wearable Electromagnetic Tracker and Orientation Sensor, Oct. 11-14, 2006, 10th IEEE International Symposium on Wearable Computers, 4 pp.*
(Continued)

Primary Examiner — Toan Le
(74) Attorney, Agent, or Firm — Howard IP Law Group, PC

(57) ABSTRACT

A measuring device including a sensor that generates data representing a detected body parameter, such as body fat, body water and weight of an individual. A portable device removably connected to the measuring device for receiving, displaying and storing the data representing the detected body parameter. The portable device may correlate the stored data with an individual user. The portable device is responsive to a personal computer for uploading the stored information thereto.

21 Claims, 4 Drawing Sheets

(51) Int. Cl.
   *G01G 19/50*   (2006.01)
   *G01G 23/37*   (2006.01)
   *G01K 1/02*   (2006.01)
   *G06F 19/00*   (2011.01)
   *A61B 5/00*   (2006.01)

(52) U.S. Cl.
   CPC ............ *G01K 1/02* (2013.01); *G06F 19/3406*
            (2013.01); *A61B 5/0002* (2013.01)

(56) References Cited

U.S. PATENT DOCUMENTS

| | | | |
|---|---|---|---|
| 8,265,901 | B2* | 9/2012 | Petrucelli ..................... 702/173 |
| 2002/0183646 | A1 | 12/2002 | Stivoric et al. |
| 2003/0023186 | A1 | 1/2003 | Ueda et al. |
| 2004/0196054 | A9 | 10/2004 | Liu et al. |
| 2005/0014113 | A1* | 1/2005 | Fleck et al. .................... 434/247 |
| 2005/0247494 | A1* | 11/2005 | Montagnino ................... 177/60 |
| 2008/0004904 | A1 | 1/2008 | Tran |
| 2008/0077620 | A1* | 3/2008 | Gilley et al. ............... 707/104.1 |
| 2009/0048070 | A1 | 2/2009 | Vincent et al. |
| 2010/0292599 | A1* | 11/2010 | Oleson et al. ................. 600/519 |
| 2011/0003665 | A1 | 1/2011 | Burton et al. |

OTHER PUBLICATIONS

Abstract of Hamaguchi et al. reference, Oct. 11-14, 2006, 2 pp.*
International Search Report dated May 15, 2012 for related application No. PCT/US 12/22978.

* cited by examiner

REMOVABLE HANDHELD UNIT

CROSS REFERENCE TO RELATED APPLICATION

This application is a continuation in part of and claims priority to U.S. patent application Ser. No. 12/942,688 entitled Device for Detecting and Displaying One or More of Body Weight, Body Fat Percentage, Blood Pressure, Pulse and Environmental Temperature, filed Nov. 9, 2010, now U.S. Pat. No. 8,265,901, which is a continuation of U.S. patent application Ser. No. 11/985,345, entitled Device for Detecting and Displaying One or More of Body Weight, Body Fat Percentage, Blood Pressure, Pulse and Environmental Temperature, filed Nov. 14, 2007, now U.S. Pat. No. 7,831,408, which claims priority to U.S. Provisional Application No. 60/859,221 filed on Nov. 15, 2006, the entire disclosures of which are hereby incorporated by reference as if being set forth in their entireties herein.

FIELD OF THE INVENTION

This application relates generally to fitness monitoring systems, and more particularly, to portable handheld fitness monitors.

BACKGROUND

Various devices, such as body weight scales, are commonly used to measure physical characteristics that may be determinative of an individual's overall fitness level. However, weight alone does not provide an accurate assessment of an individual's fitness or progress in attaining fitness. For fitness conscious individuals, body fat measurements and activity level, in addition to body weight, may improve assessment of their progress toward reaching and/or maintaining fitness goals.

Consistently monitoring and recording measured information pertaining to these parameters may be difficult and time consuming for users, especially when the user is implementing a manual means to record relevant data. Accordingly, it may be advantageous to provide a fitness and health system which allows a user, or a plurality of users, to easily and accurately track their fitness level according to a number of parameters.

SUMMARY OF THE INVENTION

According to an embodiment of the present invention, a system for monitoring and recording fitness characteristics is provided. The system includes a measuring device, such as a scale, for generating data indicative of at least one fitness parameter. A portable data storage unit is removably attached to the measuring device and comprises a processor and memory configured to receive and store the data generated from the measuring device.

In another embodiment of the present invention, a portable fitness monitoring device is provided. The device includes a processor configured to communicate with an external measuring device and a personal computer. Memory is coupled to the processor and configured to store data received from the external measuring device.

A method for measuring and storing a plurality of fitness parameters is also provided. The method comprises the steps of connecting a portable data storage unit to a fitness measuring device, providing a control signal from the data storage unit to the measuring device, the control signal operative to cause the measuring device to generate output signals proportional to at least one of the plurality of fitness parameters, storing the output signals from the measuring device in the data storage unit, and uploading the stored data from the data storage unit to a personal computer.

DETAILED DESCRIPTION OF THE INVENTION

Figure 1:
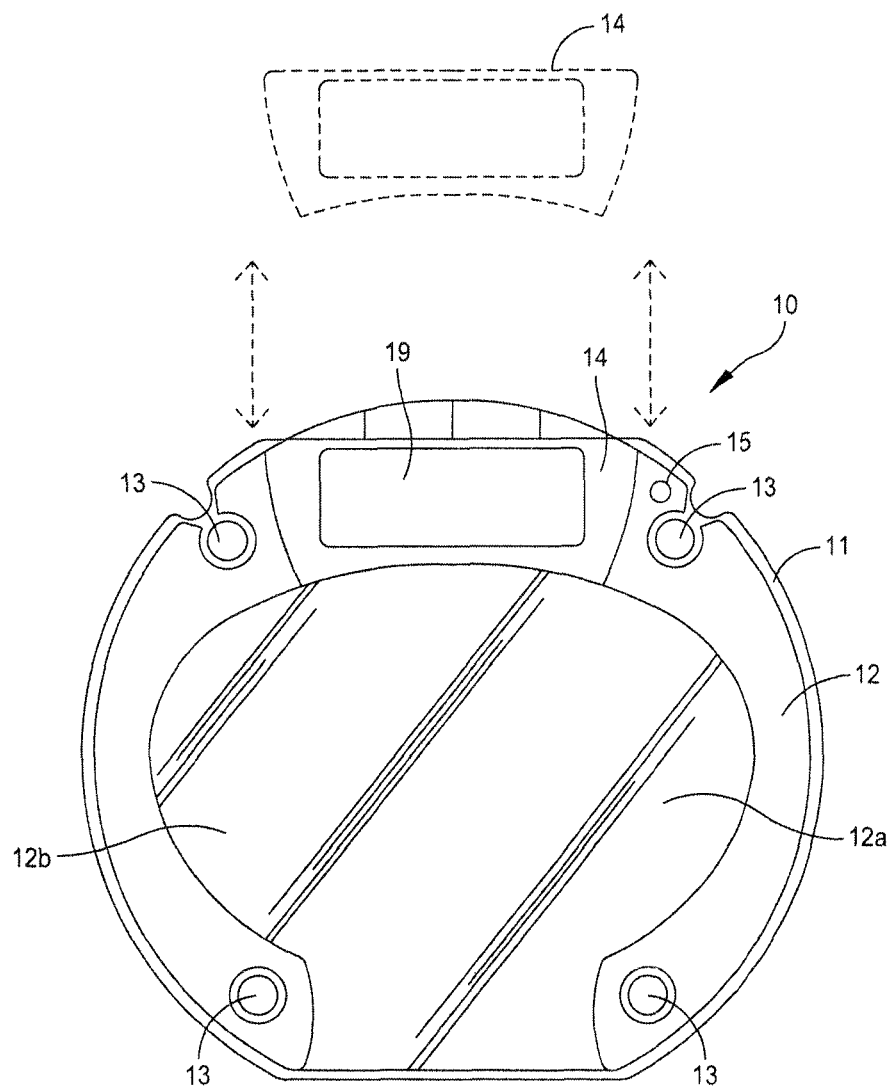
FIG. 1 illustrates an apparatus for detecting and displaying one or more body parameters in accordance with an embodiment of the present invention.

It is to be understood that the figures and descriptions of the present invention have been simplified to illustrate elements that are relevant for a clear understanding of the present invention, while eliminating, for purposes of clarity, many other elements found in typical electronic data storage, data transfer systems and fitness equipment. However, because such elements are well known in the art, and because they do not facilitate a better understanding of the present invention, a discussion of such elements is not provided herein. The disclosure herein is directed to all such variations and modifications known to those skilled in the art.

In the following detailed description, reference is made to the accompanying drawings that show, by way of illustration, specific embodiments in which the invention may be practiced. It is to be understood that the various embodiments of the invention, although different, are not necessarily mutually exclusive. Furthermore, a particular feature, structure, or characteristic described herein in connection with one embodiment may be implemented within other embodiments without departing from the scope of the invention. In addition, it is to be understood that the location or arrangement of individual elements within each disclosed embodiment may be modified without departing from the scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout several views.

Embodiments of the present invention provide a fitness measurement and tracking system comprising a portable handheld unit (HHU). The HHU may be configured to receive, process, display and store data. In one embodiment of the present invention, the HHU is configured to operatively connect to a piece of fitness equipment, such as a scale, for receiving data indicative of at least one of a user's weight, body fat, or body water composition. Once received, this data may be processed, viewed by a user, and stored within the HHU. The HHU may then be removed from the scale and used with other fitness measuring devices or equipment, wherein additional data may be processed and recorded.

The HHU is configured to interact with a personal computer (PC), allowing an individual to upload the stored fitness information from the HHU to the PC. The PC may comprise a software and/or website-based interface that aids the user in organizing and analyzing the data provided by the HHU. In this way, a user may easily track his or her fitness level without having to manually record measured data. This data may also be useful in creating or altering a fitness program to achieve desired goals.

Referring to FIG. 1, an exemplary apparatus 10 for detecting and displaying one or more body and/or fitness parameters is shown. The apparatus 10 may include a scale 11 for measuring the weight of a user and a data storage and display unit, for example, HHU 14.

The HHU 14 is configured to be removably connected to the scale 11 and may be arranged, as illustrated in FIG. 1, in a recess defined by the body of scale 11. The HHU 14 may also include a display 19 configured to display real-time measured data from the scale 11 to a user.

The scale 11 includes a platform 12, which is transparent in the illustrated embodiment, operative to support an individual who desires to be weighed. The platform 12 may rest on load cells 13 configured to output a voltage indicative of a force applied thereon (e.g. a user's weight). The scale 11 also may include a foot-activated switch or button, such as an impact-sensitive switch (not shown) for on/off control of the scale 11. The scale 11 may also include a user-identification means, for example a button 15 for selectively identifying the individual using the scale as will be set forth in greater detail herein. In an alternate embodiment, this user button 15 may be arranged on the HHU 14.

In one embodiment of the present invention, the scale 11 includes a means to measure body fat and body water percentage. This may include the use of, by way of non-limiting example, electrodes 12a, 12b, which contact the body of the user to provide a generated electrical current through the body. As will be understood by one of ordinary skill in the art, electrical current passes more easily through lean muscle than fat, and cell water percentage levels affect the resistance and the reactance of the impedance measured. Body fat and water composition may be determined from a calculation based upon the speed at which the signal passes through the body. The values for resistance and reactance as well as the subject's height and weight all serve as inputs to known equations in algorithmic form as embodied in a computer programs to yield body composition measurements such as body mass index (BMI), a measure of body fat based on height and weight that applies to both adult men and women.

While the exemplary arrangement includes features such as an HHU sized to fit into a corresponding recess in the scale, a pressure or impact sensing on/off switch, electrodes for measuring physical characteristics of a user, it is envisioned that embodiments of the present invention may exclude these features, or include any number of additional secondary features without departing from the scope of the present invention.

Figure 2:
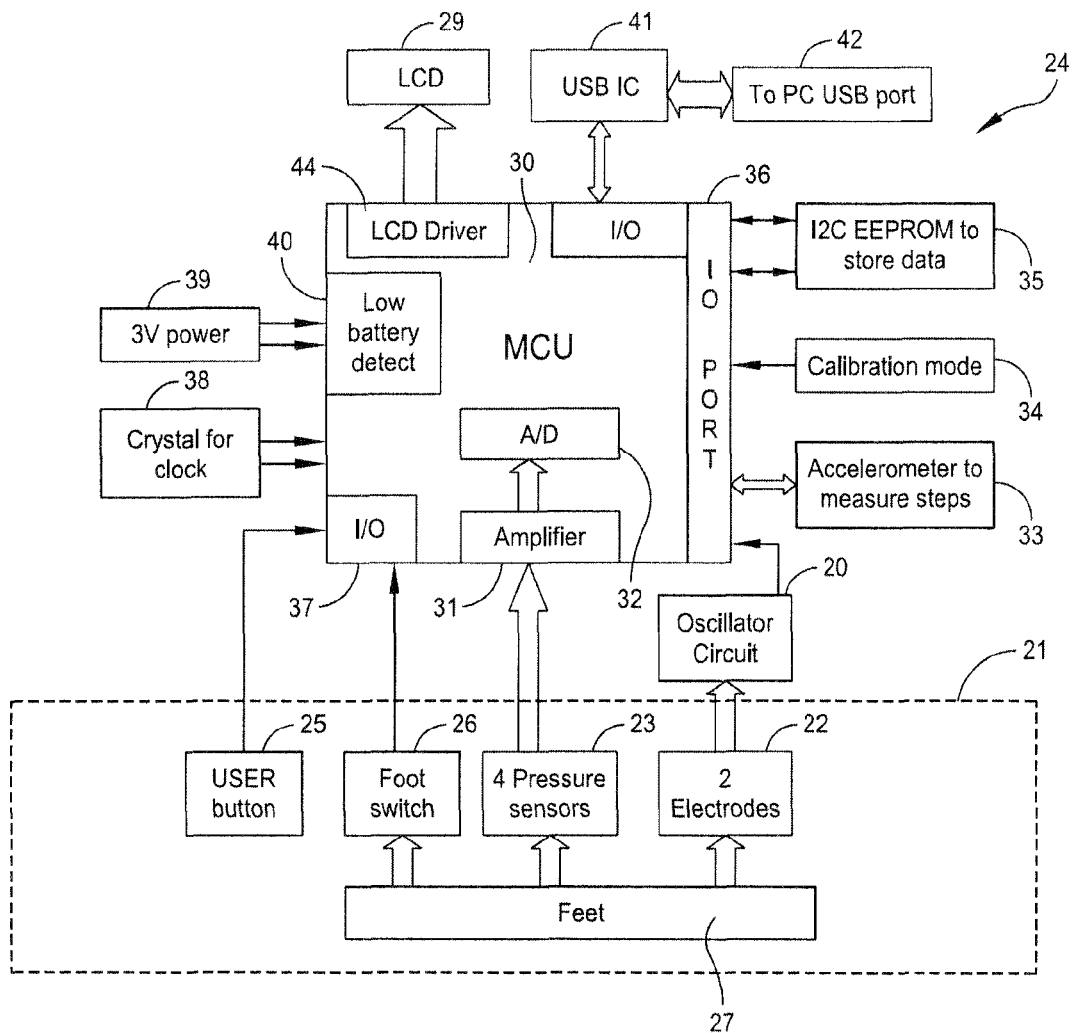
FIG. 2 is a block diagram of the apparatus of FIG. 1.

Referring generally to FIG. 2, an exemplary block diagram is provided illustrating the interface between the HHU 24 and the scale 21 in an embodiment of the present invention. As set forth above with respect to FIG. 1, the scale 21 may comprise pressure sensors or load cells 23 responsive to a weight placed on the platform 27, electrodes 22 for measuring body fat and/or water composition, on/off control switch 26, and a user-identification or interface button 25.

In the illustrated embodiment the HHU 24 is operatively connected to the scale 21 and includes a microcontroller (MCU) 30 configured to receive a variety of input signals from the scale 21. The MCU 30 may be implemented as an integrated circuit, or a small programmable computer having, for example, a processor, memory and various I/O ports, as would be understood by one of ordinary skill in the art.

As indicated above, the HHU 24 is configured to receive input signals from the load cells 23, the electrodes 22, on/off switch 26, as well as the user button 25. In the illustrated embodiment, the MCU 30 comprises circuitry, including an amplifier and an ND converter, for signal processing operations (e.g. converting an input voltage into storable data representative of an individual's body weight) performed on received signals from each of the load cells 23. As will be understood by one of ordinary skill in the art, these operations may be implemented into the HHU and/or MCU by numerous alternative circuit arrangements.

Similarly, the electrodes 22 of the scale 21 may be connected to the MCU 30 for determining body fat or body water composition as described above with respect to FIG. 1. This arrangement may include a signal oscillator 20 for providing a varying electric current to the electrodes useful for performing the water and fat composition detection process. Finally, the control signals from the on/off switch 26 and the user button 25 may be operatively connected to the MCU 30 through, for example, an I/O port 37.

HHU 24 may further include memory 35, for example EEPROM, used to store, by way of non-limiting example only, the data received from the scale 21. The memory 35 may be coupled to the MCU 30 by, for example, a data bus or port 36. The MCU 30 may also include a driver 44 for controlling a display screen located on the HHU 24, such as an LCD display 29. When the HHU 24 is coupled to the scale 21, the screen 29 may display real-time measurements made by the scale. The screen 29 may also be operative to display other data stored on the HHU 24, including previously measured data.

Also coupled to the MCU 30 may be a motion sensor or in a preferred embodiment, an accelerometer 33. A basic motion sensor may function as a counter (e.g. a step counter) to assist in the monitoring, determining, displaying, and/or storing of data from a physical activity such as walking, running, jogging, jumping rope, and the like. The accelerometer 33 may be configured as a vibration switch accelerometer, and/or may be configured such that HHU 24 may function as a pedometer when detached from the scale 21. As will be understood by one of ordinary skill in the art, a pedometer uses acceleration data indicative of the strides of an individual walking or running to generate and output an estimated distance traveled over time. This acceleration data is received by the HHU 24 from the accelerometer 33, processed, displayed and/or stored in memory.

A calibration unit 34 may also be provided for calibrating a particular user's stride to distance ratio, thus improving the accuracy of the pedometer function of the HHU 14. It will of course be understood that the display and/or additional control buttons arranged on the HHU 24 may also be provided to facilitate user control when operating in a pedometer mode, and for displaying distance/stride data when operating in said mode. The calibration unit 34, or an additional calibration unit (not shown), may also be used to calibrate the scale 21 (e.g. perform at least one zeroing function) for producing accurate weight, body fat, and water composition measurements.

The MCU 30 includes a power supply 39. By way of non-limiting example only, the power supply 39 may comprise a battery, such as a lithium ion cell. The MCU 30 may also comprise a voltage detection circuit 40, configured to detect a low battery voltage and, for example, display a warning on the screen 29. It should be noted that the replacement of the battery 39, or other loss of power to the MCU/HHU will not affect the data stored in the HHU's memory.

The HHU 24 also may include a clock with a frequency-controlling crystal 38, for keeping and/or displaying the current time. The clock also allows the HHU 24 to continuously update and store the current date. While not shown, the HHU 24 may also includes key input buttons for optionally inputting various parameters such as an individual's name, time, current and/or target weight, height and other personal data. However, it is envisioned that these operations may also be performed on a personal computer, as will be set forth in greater detail herein.

The HHU 24 comprises a means to connect to a PC 42, for example, a universal serial bus (USB) 41. The USB 41 may be implemented into the MCU 30 as an interchip USB (IC USB) and is operative to permit the transfer of data between the PC 42 and the HHU 24. This exchange of data may take place regardless of whether the HHU 24 is connected to the scale 21.

The above-described exemplary arrangement between the HHU and the scale is one of a master/slave relationship. Specifically, control of the scale, power to the scale, and the processing functions of the scale are implemented into the HHU, rather than into the scale itself. In this way, the scale will not function without being connected to the HHU. However, in an alternative embodiment, these systems may be implemented into the scale without departing from the scope of the present invention.

Figure 3:
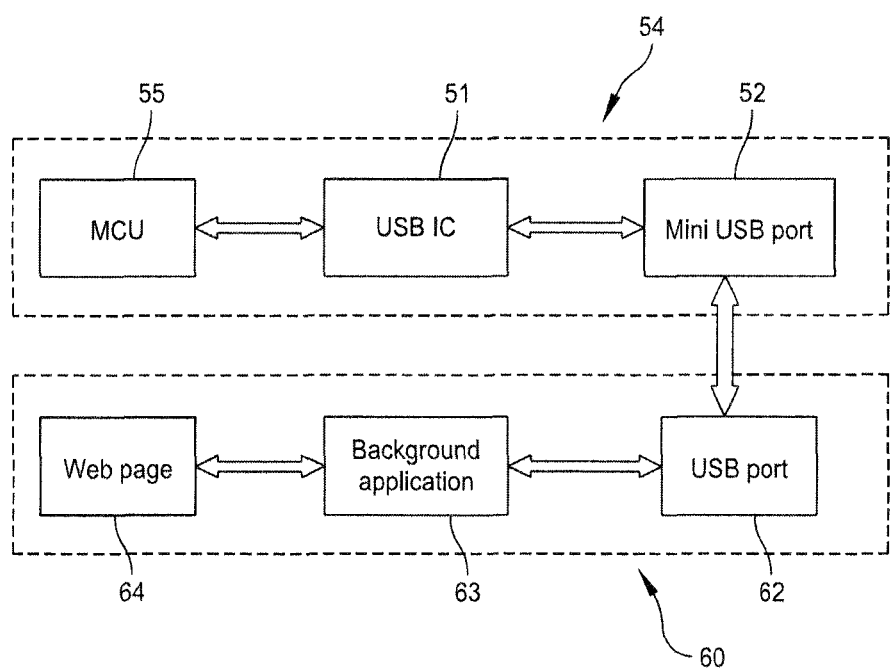
FIG. 3 is a block diagram of the apparatus of FIGS. 1 and 2 interacting with a PC.

Referring generally to FIG. 3, the interaction between an exemplary HHU 54 and a PC 60 will now be described. As described above with respect to FIG. 2, the HHU 54 may comprise an IC USB 51 having a port 52 for connecting to the USB port 62 of the PC 60. In an exemplary embodiment, the PC 60 may interface with a user through computer-readable fitness software 63 running thereon and/or through a user-accessible website 64. In one embodiment, a user may visit the specified website 64, download software 63, and register an account thereon. The downloaded software 63 may then be operative to control the downloading of data form the HHU or the uploading of data to the HHU.

As described above, multiple users can access and store data on the HHU. It is envisioned that this may be accomplished by creating separate user-accounts through the software and/or the website interface, or by adding multiple users under a single account. These users may be provided a specific user-number associated with a username for identification, or may be identified by their username alone. The user selection button on the equipment (e.g. the scale) or the HHU is operative to select between users associated with a specific HHU device.

Interaction between the HHU 54 and the PC 60 may include, by non-limiting example only, reading or writing data and/or executable instructions to the memory of the HHU. The PC readable application software and/or website may be responsive to record and store user-input information such as name, age, height, weight, address and any other desirable data and associate this data with a username or user-number. This data may be uploaded onto the HHU and used for several processes. For example, identification or user-specific data may be used by the PC and/or the HHU for saving generated fitness data which corresponds to a particular user, or for calculating a BMI using an individual user's height and weight information. Likewise, the pedometer function may utilize user-specific data, such as to calibrate an individual's stride length. It should be noted that physical characteristics, for example, a user's weight used in determining BMI and/or water composition estimations may be continuously updated each time a user is weighed, or other relevant measurement is taken.

As noted above, each measurement taken by the HHU may be stored along with the date and time the measurement was taken. This information may be downloaded to the PC when the HHU is connected thereto. In this way, the application software and/or website may organize, display, and allow a user to view data according to, for example, chronological order or over a selected time period. The program may also be operative to calculate, for example, total weight change over a given period of time, BMI change, or any number of useful functions for aiding a user in tracking and/or planning fitness goals. This flexibility allows for the precise monitoring of a user's fitness goals and/or progress.

While an embodiment of the present invention is used with a scale, it is envisioned that the HHU may be configured to communicate, receive and store data generated from any number of fitness or health devices, such as workout equipment (e.g. treadmills and weight machines), blood pressure and/or heart-rate monitors. In this way, the PC-based fitness program may be operative to combine data from each of these sources to track an individual's fitness progress or physical activity level. Information stored on the HHU in these alternate embodiments could include distance and time information, as well as weight and repetition information so a user may track his or her progress in, for example, building cardio endurance or increasing physical strength.

Figure 4:
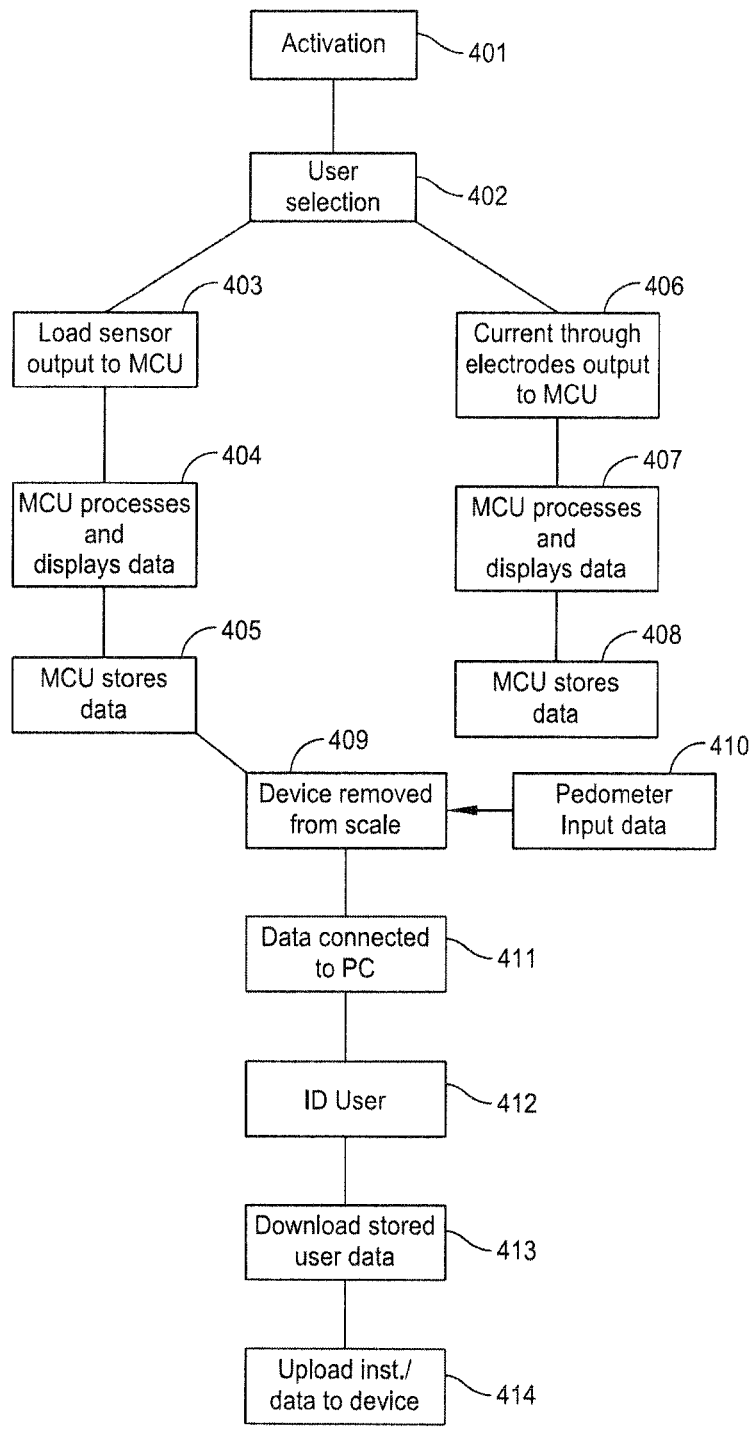
FIG. 4 is a block diagram of exemplary functions of the apparatus.

The operation of the exemplary embodiment will now be described with respect to FIG. 4. With the HHU and the scale operatively connected, the scale is activated in step 401 by, for example, tapping on the platform of the scale by the foot of the user. The foot switch will close and activate the MCU to start the measurement process. In step 402, the user may select his or her username or ID number, previously uploaded to the HHU from the PC, using the button provided on either the scale or the HHU. Once selected, the HHU will associate incoming data with the selected user, and/or utilize pre-input data specific to the user for performing various data processing operations and calculations.

With regard to the weighing function of the scale, in step 403, a signal indicative of the user's weight is provided to the MCU (i.e. to the amplifier and ND converter as set forth above). In step 404, the MCU processes the received data, which may include utilizing various calibration factors, and displays the user's weight on the LCD screen. In step 405, the weight data is stored in the memory of the HHU. This weight may be associated with the particular username or number selected in step 402.

In step 406 a body impedance measurement is taken. Specifically, after the scale has been turned on in step 401, a user may select their username or number, which is correlated with individualized user information, such as height and weight information as set forth above. This data may have been pre-programmed into the HHU either through an interface located thereon, or through the PC application and/or website and associated interface (i.e. a keyboard).

When the user stands on the electrodes, the frequency of the oscillator circuit is changed. In step 407, the MCU measures the frequency change and calculates, by way of non-limiting example only, the user's body fat, body water, muscle, BMR, and/or BMI using the user-specific information. In step 408, the resulting data will be stored in the HHU memory for future upload to the PC by the user. It should be noted that for any of these operations, the HHU can store multiple measurements, for multiple users. In this way, an HHU may not have to be connected to a PC for upload after each measurement, but rather, only periodically when the memory is full.

In step 409, the HHU is removed from the scale. Once removed, the device may be used as a pedometer as set forth above with respect to FIG. 2. Accordingly, in step 410, the HHU may utilize calibration information pertaining to stride distance, as well as data received from the accelerometer, to generate step count and distance data. As described above, this data may be associated with a specific username or number and may be displayed on the LCD screen and/or stored in memory.

In step 411, the HHU is connected to a PC, by, for example, a USB interface. The HHU may act as an HID USB device. In this way, there may be no need to install a specified driver, as the PC will recognize the HHU and communicate with standard universal commands. It should be noted that the connection between the HHU and PC may be provided while the HHU is connected to the scale without affecting its functionality. Thus, it is also envisioned that the PC may also communicate to the scale through the HHU using this same standard protocols.

In step 412, the user may be prompted by the PC (either through the fitness application running on the PC or through the website) to identify themselves. In this way, downloaded data (e.g. weight, body fat, BMI) may be immediately associated with a particular user, and only data specific to the user will be downloaded (step 413). In another embodiment of the present invention, the connection to the PC will result in the downloading of saved data corresponding to all users, and not solely the currently-identified user.

Referring generally to step 414, depending on the functionality of the scale, the HHU may communicate various instructional commands and data to the scale, for example, instructions for controlling the operation of the scale. These instructions may be uploaded to the HHC from the PC via the USB connection. Further, the user-specific information, including user name or identification number, height, age, gender, fitness level, birthday, stride length may also be uploaded to the HHU.

In an embodiment of the present invention, if data recorded in the HHU is successfully download to the PC, then HHU will delete the data from its memory, freeing space for future data storage. The HHU memory may also be selectively deleted by a user using the PC or website interface.

With respect to the username or user identification number, the PC and/or HHU may implement, by way of example only, an 8-bit username to identify a user. The PC and/or HHU may also be operative to change the scale's measuring units, for example, to kilograms, pounds, or stones.

According to an aspect of the present invention, a wired connection may be provided between scale and the HHU, when HHU is connected to the scale, as shown in FIG. 1. Alternatively, wireless communication may be used at all times. In this way, the HHU may be configured to easily communicate with a personal digital assistant (PDA), such as a handheld mobile phone, BlackBerry® wireless platform or similar device in addition to a PC. The application software installed in the device HHU, may, by way of non-limiting example, employ Physical Markup Language (PML). PML, a markup language based on XML for communicating a description of physical environments and the objects within them, their relationships to the user.

Those skilled in the art of computer programming will appreciate that the invention may be implemented in a system of computer units or processors communicatively coupled to one another over a network, such as a wide area network. "Processor", as used herein, refers generally to a computing device such as a microprocessor having a CPU. A CPU generally includes an arithmetic logic unit (ALU), which performs arithmetic and logical operations, and a control unit, which extracts instructions (e.g., code) from memory and decodes and executes them, calling on the ALU when necessary. "Memory", as used herein, refers to one or more devices capable of storing data, such as in the form of chips, tapes, disks or drives. Memory may take the form of one or more random-access memory (RAM), read-only memory (ROM), programmable read-only memory (PROM), erasable programmable read-only memory (EPROM), or electrically erasable programmable read-only memory (EEPROM) chips, by way of further non-limiting example only. Memory may be internal or external to an integrated unit including a processor. Memory may be internal or external to an integrated unit including a personal computer. Memory unit preferably stores a computer program, e.g., sequence of instructions being operable by the processor.

While the present invention has been described with reference to the illustrative embodiments, this description is not intended to be construed in a limiting sense. Various modifications of the illustrative embodiments, as well as other embodiments of the invention, will be apparent to those skilled in the art on reference to this description. It is expressly intended that all combinations of those elements that perform substantially the same function in substantially the same way to achieve the same results are within the scope of the invention. Substitutions of elements from one described embodiment to another are also fully intended and contemplated.

What is claimed is:

1. A system for monitoring and recording fitness characteristics, said system comprising:
   a measuring device for generating data indicative of a plurality of fitness parameters, and
   a portable data storage unit configured to be connected and disconnected from the measuring device, the data storage unit comprising a processor and memory and configured to receive and store the data generated from the measuring device,
   wherein the data storage unit is configured to receive and store information including multiple user identifiers, user-specific information and the data indicative of the plurality of fitness parameters associated with each multiple user identifier, and
   wherein the data storage unit is configured to, responsive to selection of one of the multiple user identifiers, provide access only to stored data indicative of the plurality of fitness parameters associated with the selected user identifier.

2. The system of claim 1, wherein the processor is responsive to a user-input for identifying an individual using the measuring device.

3. The system of claim 1, wherein the data storage unit is configured to communicate with an external computer.

4. The system of claim 3, wherein the data storage unit is configured to communicate the stored data to the external computer.

5. The system of claim 4, wherein the user identifier and user-specific information are communicated to the storage unit by the external computer.

6. The system of claim 4, wherein the external computer is configured to organize and display the data received from the data storage unit.

7. The system of claim 6, wherein the data is organized and displayed according to a user identified with the data.

8. The system of claim 1, wherein the processor is operative to control the function of the measuring device.

9. The system of claim 1, wherein the measuring device is a scale configured to measure and output data indicative of at least one of body weight, body fat and body water composition.

10. A portable fitness monitoring device comprising:
a processor configured to communicate with an external measuring device and a personal computing device, and
a memory coupled to the processor and configured to store data indicative of a plurality of fitness parameters received from the external measuring device,
wherein the memory is configured to receive and store information including multiple user identifiers, user-specific information and the data indicative of the plurality of fitness parameters associated with each multiple user identifier, and
wherein the processor is configured to, responsive to selection of one of the multiple user identifiers, provide access only to stored data indicative of the plurality of fitness parameters associated with the selected user identifier.

11. The portable fitness monitoring device of claim 10, further comprising a viewing screen.

12. The device of claim 11, wherein the processor is operative to display the data received from the external measuring device on the viewing screen.

13. The device of claim 10, wherein the portable fitness monitoring device is adapted to be attachable and detachable from said external measuring device and adapted to be housed in a recess defined in said external measuring device.

14. The device of claim 10, further comprising an accelerometer, the accelerometer operative to generate an output signal indicative of the strides of a user such that the device functions as a pedometer.

15. A method for measuring and storing a plurality of fitness parameters, said method comprising the steps of:
connecting a portable data storage unit to a fitness measuring device, the portable data storage storing information including multiple user identifiers and user-specific information;
providing a control signal from the data storage unit to the measuring device, the control signal operative to cause the measuring device to generate output signals proportional to the plurality of fitness parameters;
associating the output signals with a respective one of the multiple user identifiers;
storing the output signals from the measuring device in the data storage unit, and
uploading the stored data from the data storage unit to a personal computer,
wherein the stored data indicative of the plurality of fitness parameters associated with one of the multiple user identifiers is accessible only responsive to selection of the one of the multiple user identifiers.

16. The method of claim 15, wherein the step of uploading the stored data to a personal computer further comprises the step of disconnecting the data storage unit from the measurement device and connecting the data storage unit to the computer.

17. A portable fitness monitoring device comprising:
a processor configured to communicative with an external measuring device and a personal computing device,
a memory coupled to the processor and configured to store data indicative of a plurality of fitness parameters received from the external measuring device,
an accelerometer operative to generate an output signal indicative of the strides of a user such that the device functions as a pedometer, and
a calibration unit for calibrating an individual user's stride to distance ratio.

18. The device of claim 17, wherein the processor is responsive to a user-input for identifying an individual using the measuring device.

19. The device of claim 18, wherein the processor is configured to associate the stored data with a user identifier.

20. The device of claim 19, wherein the processor is configured to communicate the stored data to the personal computing device.

21. The device of claim 19, wherein the processor is configured to associate the stored data with a plurality of user identifiers.

* * * * *